(12) United States Patent
Bernstein et al.

(10) Patent No.: US 6,379,357 B1
(45) Date of Patent: Apr. 30, 2002

(54) MODULAR SPINAL SYSTEM

(75) Inventors: Avi Bernstein, Wilmette, IL (US); Stewart Young, Memphis, TN (US); Andrew Simonton, Las Vegas, NV (US); David Miller, Eads, TN (US); David L. Brumfield, Southhaven, MS (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/718,915

(22) Filed: Nov. 22, 2000

Related U.S. Application Data (63) Continuation of application No. 08/798,855, filed on Feb. 12, 1997, now Pat. No. 6,176,861, which is a continuation-in-part of application No. 08/707,025, filed on Sep. 10, 1996, now Pat. No. 6,004,322, which is a continuation of application No. 08/328,833, filed on Oct. 25, 1994, now abandoned.

(51) Int. Cl.[7] ............................................. A61B 17/70
(52) U.S. Cl. .......................................... 606/61; 606/73
(58) Field of Search .............................. 606/60, 61, 72, 606/73

(56) References Cited

U.S. PATENT DOCUMENTS

| | | | |
|---|---|---|---|
| 2,439,995 | A | 4/1948 | Thrailkill |
| 2,627,855 | A | 2/1953 | Price |
| 4,569,338 | A | 2/1986 | Edwards |
| 4,648,388 | A | 3/1987 | Steffee |
| 4,854,311 | A | 8/1989 | Steffee |
| 4,887,585 | A | 12/1989 | Nutt |
| 4,946,458 | A | 8/1990 | Harms et al. |
| 4,987,892 | A | 1/1991 | Krag et al. |
| 5,024,213 | A | 6/1991 | Asher et al. |
| 5,047,029 | A | 9/1991 | Aebi et al. |
| 5,053,034 | A | 10/1991 | Olerud |
| 5,084,049 | A | 1/1992 | Asher et al. |
| 5,113,685 | A | 5/1992 | Asher et al. |
| 5,129,899 | A | 7/1992 | Small et al. |
| 5,129,900 | A | 7/1992 | Asher et al. |
| 5,196,014 | A | 3/1993 | Lin |
| 5,217,461 | A | 6/1993 | Asher et al. |

(List continued on next page.)

FOREIGN PATENT DOCUMENTS

| | | |
|---|---|---|
| EP | 0 468 264 | 1/1992 |
| EP | 0 553 424 | 8/1993 |
| EP | 0 611 116 | 8/1994 |
| FR | 1 136 123 | 12/1956 |
| FR | 1 293 395 | 12/1956 |
| FR | 2 615 095 | 5/1987 |
| FR | 2 671 966 | 1/1992 |
| GB | 2 090 745 | 7/1982 |

OTHER PUBLICATIONS

Brochure for *Kambit Offset Bolt*, Smith & Nephew Richards, undated.

*Primary Examiner*—David O. Reip
(74) *Attorney, Agent, or Firm*—Woodard, Emhardt, Naughton Moriarty & McNett (57) ABSTRACT

A modular bone fastener system for use with a longitudinal member, such as a plate, having a fastener with a threaded lower potion for engaging a spinal element and an upper portion adapted to receive a headpiece. The headpiece is adapted to mate with the upper portion of the fastener and to engage a longitudinal member. A plurality of headpieces having angulated projections, lateral sections, and angulated lateral sections, all of which are adapted to engage a longitudinal member and overcome angular and translational misalignment of the fastener, may also be provided. The headpieces of some connectors are configured to permit angulation of a bore fastener relative to the connector.

7 Claims, 9 Drawing Sheets

U.S. PATENT DOCUMENTS

| | | |
|---|---|---|
| 5,242,443 A | 9/1993 | Kambin |
| 5,257,994 A | 11/1993 | Lin |
| 5,261,909 A | 11/1993 | Sutterlin et al. |
| 5,275,601 A | 1/1994 | Gogolewski et al. |
| 5,344,422 A | 9/1994 | Frigg |
| 5,470,333 A | 11/1995 | Ray |
| 5,474,551 A | 12/1995 | Finn et al. |
| 5,480,440 A | 1/1996 | Kambin |
| 5,487,744 A | 1/1996 | Howland |
| 5,501,684 A | 3/1996 | Schlapfer et al. |
| 5,520,688 A | 5/1996 | Lin |
| 5,609,592 A | 3/1997 | Brumfield et al. |
| 5,693,053 A * | 12/1997 | Estes .......................... 606/61 |

* cited by examiner

MODULAR SPINAL SYSTEM

CROSS REFERENCE TO RELATED APPLICATIONS

This application is a continuation of U.S. patent application Ser. No. 08/798,855, filed Feb. 12, 1997, now U.S. Pat. No. 6,176,861; which is a continuation-in-part of U.S. patent application Ser. No. 08/707,025, filed Sep. 10, 1996, now U.S. Pat. No. 6,004,322; which is a file wrapper continuation of U.S. patent application Ser. No., 08/328,833, filed Oct. 25, 1994, now abandoned.

FIELD OF THE INVENTION

The present invention relates to a method and apparatus which is used to retain spinal elements in spatial relationship. More particularly, a modular pedicle screw assembly of the invention consists of a base fastener and connecting headpieces which are varied in length and angularity in order to provide a clinician a greater degree of flexibility in stabilizing the spine when performing spinal,fusions in the cervical, thoracic, and lumbar regions.

BACKGROUND OF THE INVENTION

Important considerations for spinal instrumentation used to promote spinal fusion are safe insertion, rigid fixation, and ease and adaptability of implantation. Historically, Harrington rods were an early type of spinal instrumentation used to stabilize the thoracic and the upper lumbar regions to obtain correction and stability for fusion. This instrumentation involved long rods attached to hooks, which were inserted over the bony arches (lamina) of the spinal canal. The instrumentation was subject to failure when the hooks either broke the lamina or became displaced and thus, the intended stabilization and correction was lost. Other rod systems have been developed which employ rod-screw connectors. One example is the TSRH® Spinal System available from Danek Medical Inc., 1800 Pyramid Place, Memphis, Tenn. 38132, (800) 93-DANEK. Even with current improved systems remains the challenge of attachment of the rods to the spine.

Other spinal instrumentation systems include the use of a longitudinal member, such as a plate, to interconnect a series of pedicle screws such as that disclosed in U.S. Pat. No. 5,129,899 issued to Small. In this system, the clinician must strive to place the series of pedicle screws into the bone in longitudinal alignment with as little lateral displacement and angular deflection as possible so that the plate may be attached to the series of pedicle screws in order to achieve a solid biomechanical relationship. However, due to variances in the spinal column or imperfect placement by the clinician, the screws are often inserted at an angle or must be placed laterally outside the longitudinally axis defined by the plate and other screws. While slight angular deviations of screw placement may be overcome by the use of contoured washers, larger angular deflections and the problems associated with lateral displacement of the pedicle screws cannot be overcome by the instrumentation disclosed in the Small patent. Moreover, the use of such contoured washers adds to the number of parts to be manipulated by the surgeon.

The development of the Kambin Offset Bolt (Smith & Nephews Richard, Inc.) for use with the device disclosed in the Small, et al. patent allows greater flexibility when the pedicle screws cannot be placed in the desired longitudinal relationship. The Kambin Bolt has a double threaded shank with an upper portion offset 6 mm from the axis of the lower portion. This offset bolt, however, has several drawbacks. First, insertion of the offset bolt requires a larger area of clearance to obtain insertion. This often leads to insertion difficulty when the bolt interferes with the spinal retractors, other elements of the spine, or other screws which have already been implanted. This interference can cause other implanted screws to loosen when impinged. In addition, once in place, the offset bolt can only overcome translational misalignment, but not angular misalignment of the pedicle screws.

U.S. Pat. No. 5,129,900 to Asher, et al. discloses a connector for pedicle screws and spinal rods. Lateral deviations may be cured by the use of connector members which include oblong openings. (Col. 4 lines 54–67). Like the offset screw taught by the Small patent, however, the device disclosed in the Asher patent cannot overcome the difficulties associated with angular misalignment.

Accordingly, a need has remained for devices which conveniently compensate for both translational and angular misalignment of bone fasteners relative to spinal devices such as rods and plates.

SUMMARY OF THE INVENTION

The present invention preserves the advantages of using a bone screw and longitudinal member while providing new features and advantages not found in the previous instrumentation. Specifically, the invention overcomes both translational misalignment and angular misalignment by providing a modular screw system having a fastener adapted to receive a plurality of headpieces with various angular and lateral length configurations which are, in turn, connected to a longitudinal member or members to obtain rigid stabilization of the spine.

In one embodiment of the present invention, a pedicle screw is provided having an exterior thread along its lower portion and an upper portion adapted to securely receive a headpiece. The headpiece includes a neck which has a bore adapted to mate with the upper portion of the fastener and further includes a projection which terminates in a connector which is adapted to engage a longitudinal member such as a plate or rod.

In another embodiment of the present invention, the upper portion of the pedicle screw is frusto-conical in shape with a fluted outer or "male" surface; the headpiece including a corresponding inner or "female" portion. Mating the two components in this manner provides greater lateral and rotational stability.

In yet another embodiment of the present invention, an angulated headpiece is provided. The headpiece of this embodiment includes a neck portion having a projection which extends out of the neck at various angulations and terminates with a connector for engaging a longitudinal member. Angulating the projection allows for the correction of angular misalignment of the fastener.

In still another embodiment of the present invention, a translational headpiece is provided. The headpiece of this embodiment includes lateral sections which extend outwardly from the neck and may range in length from about 5 millimeters to 3 centimeters. The lateral sections also terminate in a connector for engaging a longitudinal member and allow for the correction of translational misalignment of the fastener.

In a further embodiment of the present invention, an angulated translational headpiece is provided. The headpiece of this embodiment includes angulated lateral sections which extend outwardly from the neck of the headpiece at various angles and lengths. These sections also terminate in a connector of both angular and translational misalignment of the fastener.

Not only does the present invention provide the clinician with the flexibility and adaptability needed to overcome difficult misalignment problems, it offers the patient a number of safety benefits as well. First, the present invention reduces the stress placed on both the placed fastener and patient's bone by reducing the need to manipulate misaligned fasteners. Second, the integrity of the patient's bone is maintained by eliminating the number of placements into the bone since misaligned fasteners do not need to be removed and/or relocated when the present invention is used by the clinician.

Accordingly, an object of the present invention is to provide a modular screw system and method of implanting the same which is more flexible, safer and easier to implant than present spinal instrumentation and methods.

Another objection of the present invention is to provide a modular screw system and method which can overcome translational misalignment of the fastener.

A further object of the present invention is to provide a modular screw system and method which can overcome angular misalignment of the fastener.

Yet another object of the present invention is to provide a modular screw system and method which can overcome both translational and angular misalignment of the fastener.

Still another object of the present invention is to provide a modular screw system and method which uses a fastener and headpiece having corresponding mating shapes in order to improve both the lateral and rotational stability between the two pieces.

Yet a further object of the present invention is to provide a modular screw system and method that can be used in combination with existing screw system employing either longitudinal plates or rods.

BRIEF DESCRIPTION OF THE DRAWINGS

These and other features, objects and advantages of the present invention will become apparent from the following description and drawings wherein like reference numerals represent like elements in the several views, and in which.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
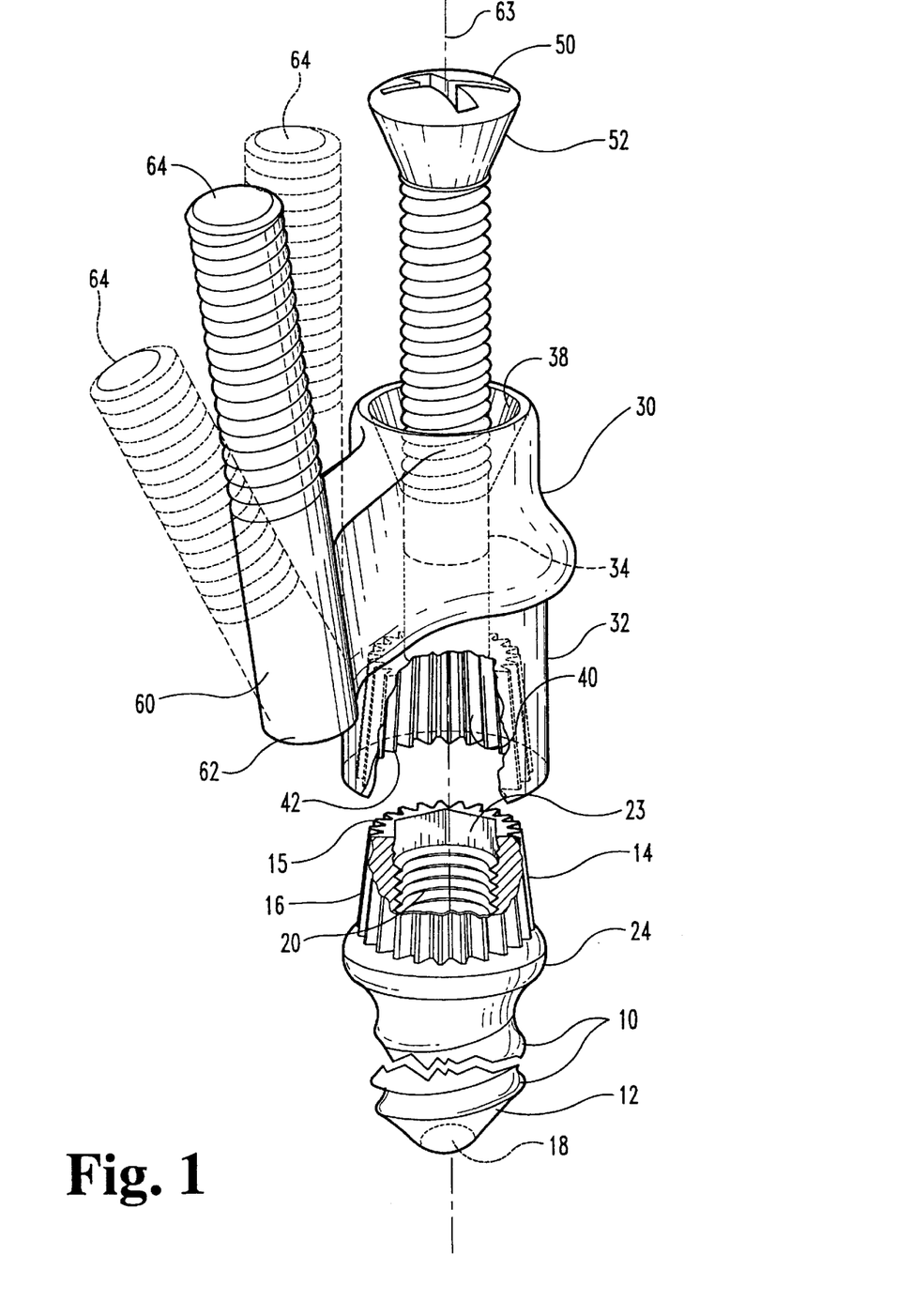
FIG. 1 is a perspective view of an embodiment using an angulated headpiece having a connector adapted to engage a plate-like longitudinal member and with portions removed to reveal aspects of the invention.

In accordance with a preferred embodiment as shown in FIG. 1, the modular pedicle screw system includes a pedicle screw or fastener 10; a headpiece 30 which is adapted to engage fastener 10; and, a locking element 50 which mechanically affixes fastener 10 to headpiece 30.

Figure 2:
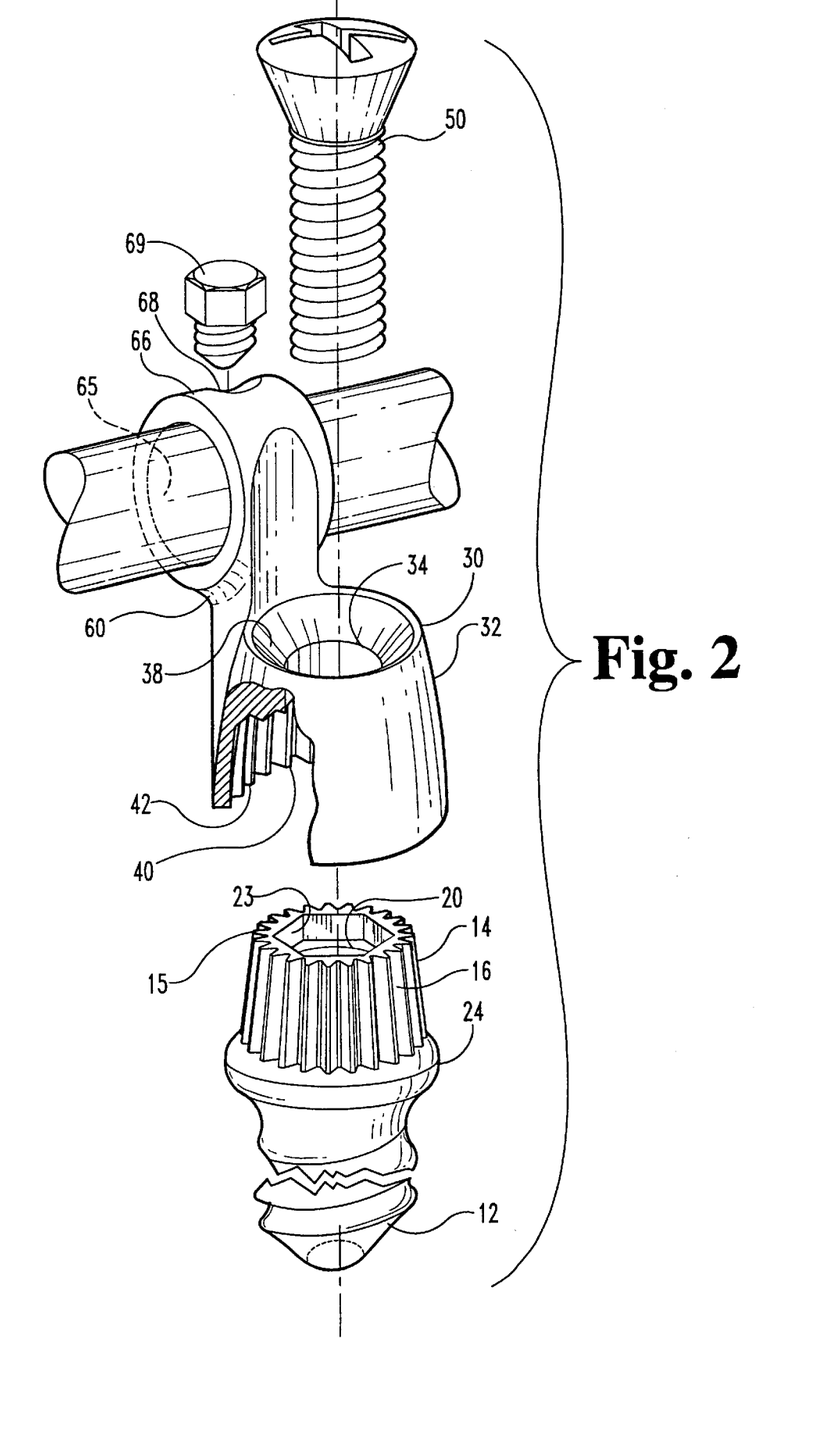
FIG. 2 is a perspective view of the embodiment shown in FIG. 1 which is designed to work with a rod-like longitudinal member and has portions removed to reveal aspects of the invention.

Fastener 10 also includes a threaded lower portion 12 for engaging a spinal element and an upper portion 14 which is adapted to allow for the mechanical affixment of fastener 10 to headpiece 30. One suitable configuration for upper portion 14 that provides rotational and lateral stability is a frusto-conical shape 15 having fluted edges 15 on its outer surface as shown in FIGS. 1 and 2. Upper portion 14 may also be configured as a cylinder, square, hex, or in other shapes persons of ordinary skill would recognize.

Fastener 10 further includes a bore 18 which allows fastener 10 to be cannulated during insertion. The diameter of bore 18 is increased near upper portion 14 to form an internal threaded portion 20 for receiving locking element 50. Bore 18 of fastener 14 may also terminate in a hex-shaped recess 23 which provides a surface that can engage a suitable insertion tool (not shown). A shoulder 24 may also be provided which acts as a stop that limits the depth fastener 10 can be inserted.

As shown in FIGS. 1 and 2, headpiece 30 includes a neck portion 32 having cylindrical aperture 34 with engagement surface 38. Engagement surface 38 is dimensioned so as to allow head 52 of locking element 50 to form a secure fit with upper surface 38 when inserted.

Neck 32 further includes a recess 40 which is adapted to mate with upper portion 14 of fastener 10. In the embodiment using a frusto-conical shape, recess 40 would have a mating fluted surface 42 and would be configured to mate with the frusto-conical shape 15. Recess 40 may also have other configurations designed to mate with the other shapes described above. By mating upper portion 14 of fastener 10 with recess 40 of headpiece 30 both lateral and rotational stability between the two pieces is achieved.

There are a number of variations of headpiece 30 which are built upon the basic structure of headpiece 30 as described above. One is an angulated headpiece 60 (also shown as headpiece 30 of FIGS. 1 and 2), which includes a projection 62 that extends out of neck 32 as shown in FIG. 1. Projection 62 terminates in a connector which can be either a threaded shank 64 (as shown in FIG. 1) or a rod connector 66 having an engagement aperture 65, a threaded bore 68 and a locking screw 69 (as shown in FIG. 2), which are, in turn, adapted to secure a longitudinal member such as plate of design similar to that disclosed in the Small, et al. patent or a rod 62 of a design similar to that disclosed in the Asher, et al. patent, respectively.

Other headpiece variations, which will be described below, may also terminate in these connectors, but persons of ordinary skill in the art would also recognize that the headpieces may be adapted to work with other types of longitudinal support members as well. Since one of the purposes of the invention is to overcome angular misalignment, projection 62 of the angulated headpiece 60 is angled with respect to centerline 63 of headpiece 60 as shown in FIG. 1. The degrees of angulation of projection 62 should vary but should include angulations in the range of about 5° to 45°.

Figure 3:
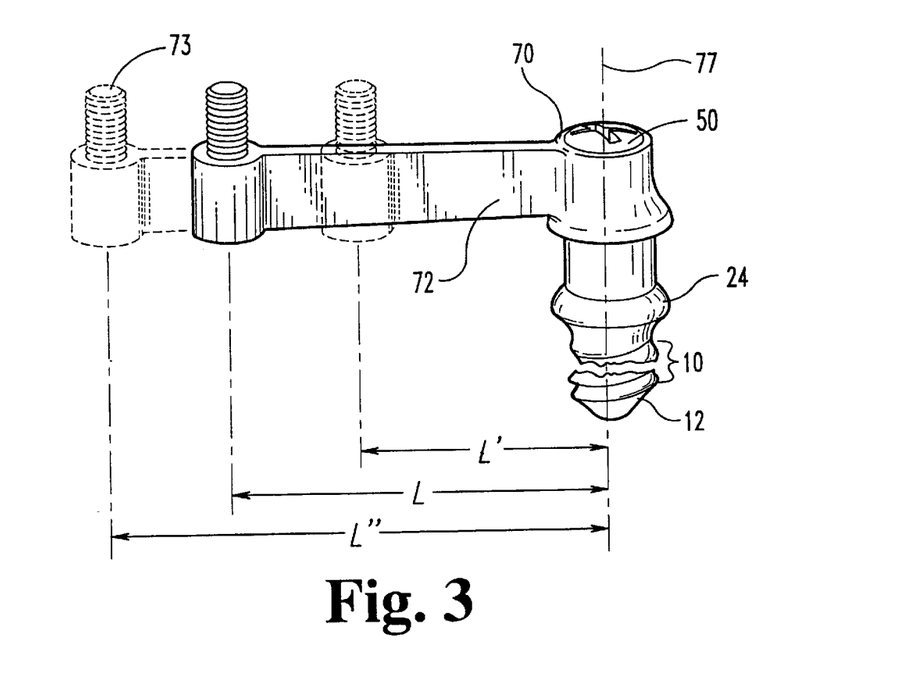
FIG. 3 is a perspective view of an embodiment having a translational headpiece consisting of a plurality of lateral length sections.

FIG. 3 illustrates translational headpiece 70. Translational headpiece 70 includes lateral section 72 which extends outwardly from centerline 77 of headpiece 70 and terminates with a connector 73 as described above. To provide the greatest degree of flexibility to a clinician, the length (LL', L") of section 72 should vary and include typical lengths ranging from about 5 millimeters to 3 centimeters.

Figure 4:
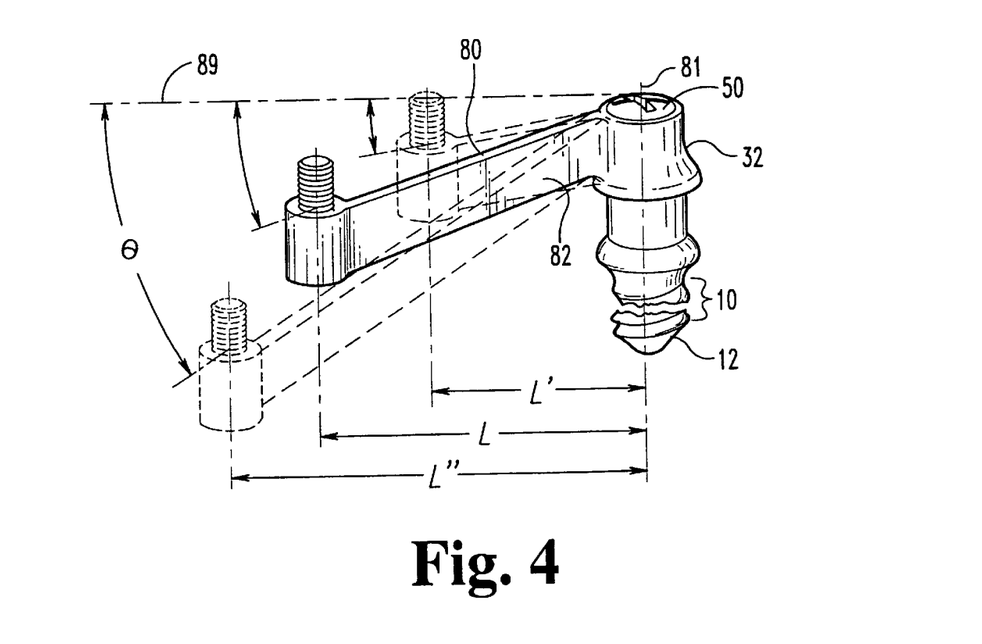
FIG. 4 is a perspective view of an embodiment having an angulated translational headpiece consisting of a plurality of angular and lateral length configurations.

As shown in FIG. 4, another headpiece embodiment is an angulated translational headpiece 80, which is a combination of the previously described headpiece embodiments. Headpiece 80 includes lateral section 82 which extends outwardly from centerline 81 of headpiece 80. In addition, section 82 is also angulated with respect to a horizontal axis shown as line 89. The degrees of angulation (θ) should vary and may include angulations in the range of about 2° to 45°. The lengths (LL', L") of section 82 should also vary as described above.

Figure 5:
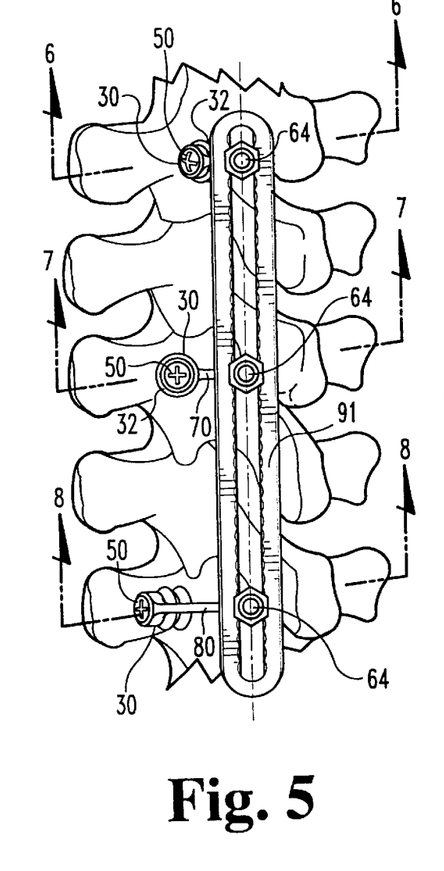
FIG. 5 is a posterior view of a spinal section in which an apparatus constructed in accordance with the present invention has been implanted.

By providing a modular pedicle screw system with a fastener that accommodates a plurality of at least three different headpieces with various lateral section lengths, various angulated projections and a combination of the two provides the clinician with a system which can overcome many of the misalignment problems encountered during the implantation of spinal instruments as shown in FIG. 5.

Figure 6:
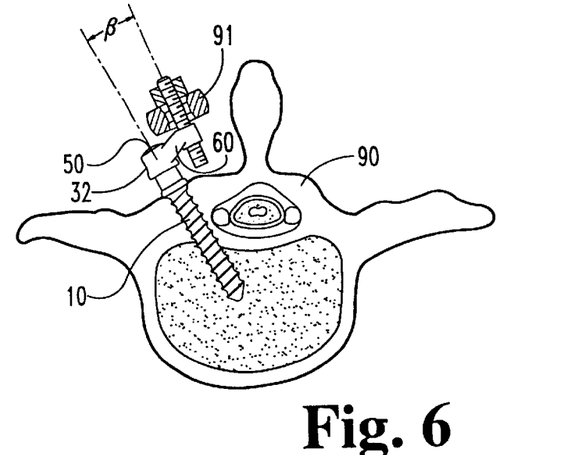
FIG. 6 is an enlarged view, partly in section taken generally along the line 6—6 of FIG. 5, illustrating an embodiment threaded into a spinal element and overcoming angular misalignment of the fastener.

In situations involving primarily angular misalignment as shown in FIGS. 5 and 6, fastener 10 will first be secured to a spinal element 90 by a suitable insertion tool which may be a hex-shaped wrench or a wrench having a bore designed to mate with upper portion 14. The clinician will then select one of the angulated headpieces 60 which best compensates for the angular misalignment, if any, and returns the threads shank or rod connector to a position where it is once again in longitudinal alignment wit the longitudinal member 91 and other fasteners. The headpiece and fastener will then be secured together by set screw 50, and ultimately, a longitudinal member will be securingly retained by a connector as previously described.

Figure 7:
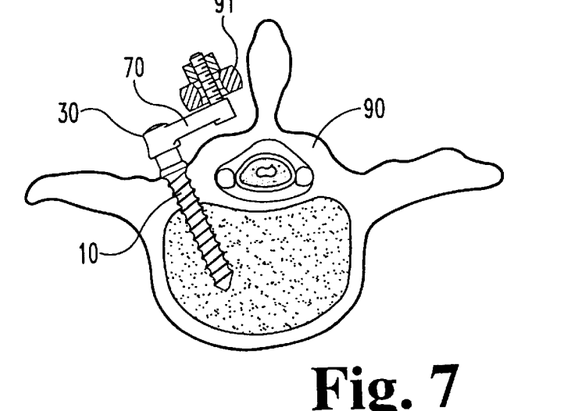
FIG. 7 is an enlarged view, partly in section taken generally along the line 7—7 of FIG. 5, illustrating an embodiment threaded into a spinal element and overcoming lateral misalignment of the fastener.

In situations involving primarily translational misalignment, as shown in FIGS. 5 and 7, fastener 10 will first be secured to a spinal element 90. The clinician will then select one of the translational headpieces 70 which best compensates for the misalignment and returns connector 73 to a position of proper alignment for securing a longitudinal member 91. Moreover, by first inserting a fastener that does not include a lateral section, an potential interference from spinal retractors, other elements of the spine, or the other screws which have already been implanted can be eliminated. Thus, the clinician can use the present invention in areas which may not be accessible to other offset bolts currently available.

Figure 8:
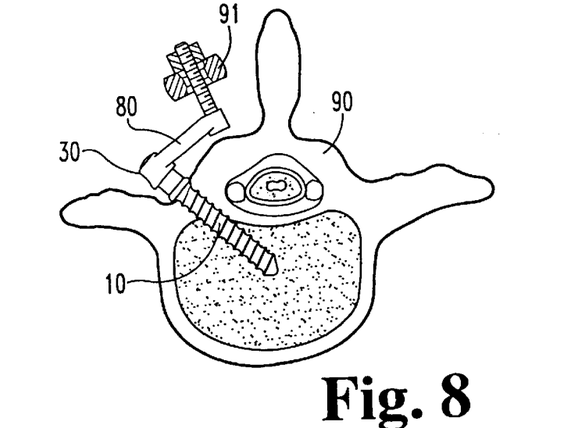
FIG. 8 is an enlarged view, partly in section taken generally along the line 8—8 of FIG. 5, illustrating an embodiment threaded into a spinal element and overcoming both angular and lateral misalignment of the fastener.

In situations presenting both translational and angular misalignment, as shown in FIGS. 5 and 8, an angulated translational headpiece 80 is used. Again, fastener 10 is first inserted into spinal element 90. The clinician then selects the appropriate headpiece with the correct lateral length and angular deflection which will compensate for the misalingment as shown in FIGS. 5 and 8.

Figure 9:
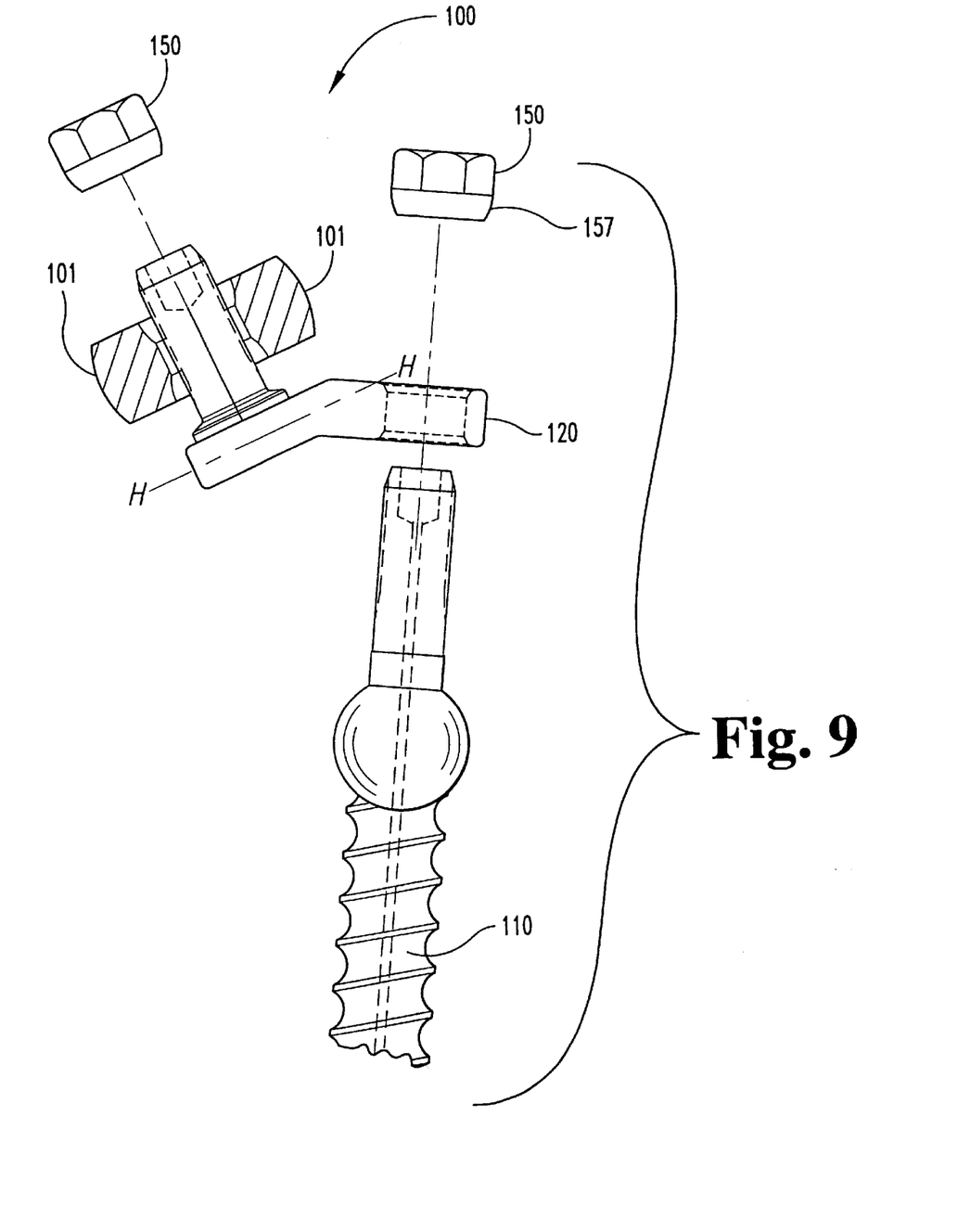
FIG. 9 is a partial side cross-sectional view of a system of this invention.

The present invention also provides spinal fixation systems including a spinal plate, a bone fastener and an offset connector or bracket for relating the plate to the fastener. Conveniently, the bracket of this invention can also be incorporated into known plate and screw systems such as the DYNALOK® Spinal System and the Danek® Plate and Screw System available from Danek Medical, Inc. 1800 Pyramid Place, Memphis, Tenn. 38132 (800-93-DANEK). In one embodiment, a spinal fixation system 100 for maintaining vertebrae in a desired relationship is provided as shown in FIG. 9. The system 100 includes spinal plate 101 shown in cross-section, a bracket 120, a bone screw or bolt 110 and a pair of internally threaded fasteners, such as nuts 150.

Figures 10, 11:
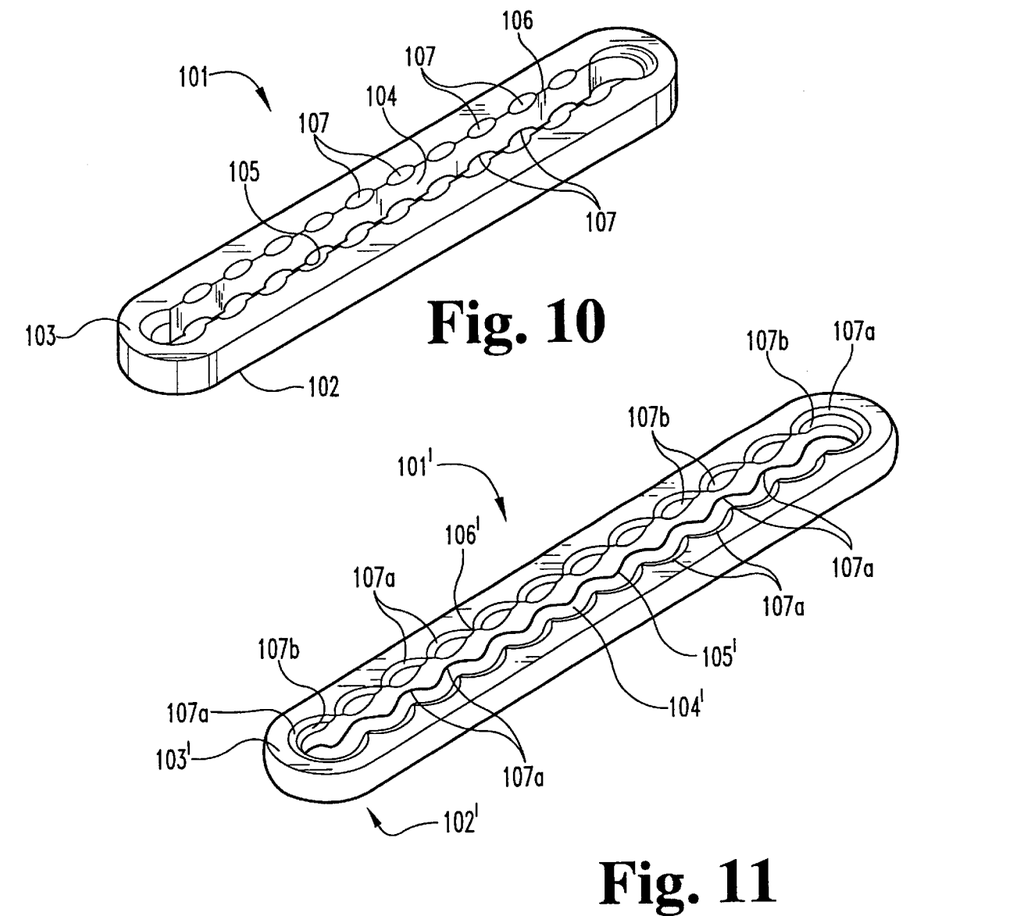
FIG. 10 is a perspective view of a spinal plate.
FIG. 11 is a perspective view of another spinal plate.

Referring now to FIG. 10, the plate element 101 is preferably a substantially rigid, elongated spinal plate having a length for spanning the vertebrae. The plate 101 includes a bottom side 102 for facing the vertebrae and an opposite top side 103 extending generally parallel to the bottom side 102. An elongated slot 104 is defined between the bottom side 102 and the top side 103. The slot 104 preferably extends substantially along the length of the plate 101 and has a lower edge 105 at the intersection of the slot 104 and the bottom surface 102 and an upper edge 106 at the intersection of the slot 104 and the top surface 103. The plate 101 also preferably includes a number of scallops 107 formed at the lower edge 105 and the upper edge 106 of the slot 104. This is similar to the bone plate of the DANEK® Plate and Screw System marketed by Danek Medical, Inc.

Another plate embodiment is contemplated as depicted in FIG. 11. This plate 101' includes a first set of scallops 107a and a second set of scallops 107b. Each of the sets of scallops 107a, 107b are formed in both the upper 106' and lower 105' edges. The first set of scallops 107a has a spherical radius that is different from the second set 107b as described in U.S. Pat. No. 5,209,751 to Farris et al., the disclosure of which is incorporated herein by reference. A similar plate is marketed by Danek Medical, Inc. for its DYNALOK® Spinal System.

Figure 12:
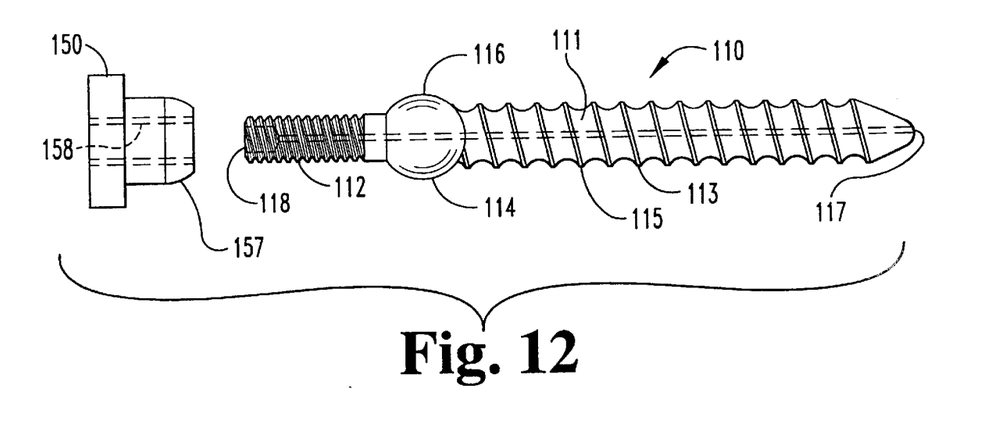
FIG. 12 is a side elevational view of a bone bolt.

The system also includes a bone fastener such as a bone screw or a bone bolt. Preferably, double hex screws such as marketed by Danek Medical, Inc. are used. Most preferably, the bone fastener is a double threaded bolt such as the Danek Medical DYNALOK® cannulated bolt. Referring now to FIG. 12, a bone bolt 110 has an elongated shaft 111 having a first threaded portion 112, a second threaded portion 113 and an intermediate portion 114 between the first 112 and second 113 threaded portions. The second threaded portion 113 includes a number of threads 115 adapted to engage the bone of the vertebra. The intermediate portion 114 of this embodiment has an integral rigid upper arcuate surface 116 facing toward the first threaded portion 112. Preferably the bolt 110 is cannulated to include a bore 117 extending through the entire length of the bolt 110. Preferably the bolt 110 is also provided with an insertion tool cavity 118 in an end of the first portion 112. In one embodiment, the cavity 118 is hexagonal in configuration for engaging an insertion tool.

Figure 13:
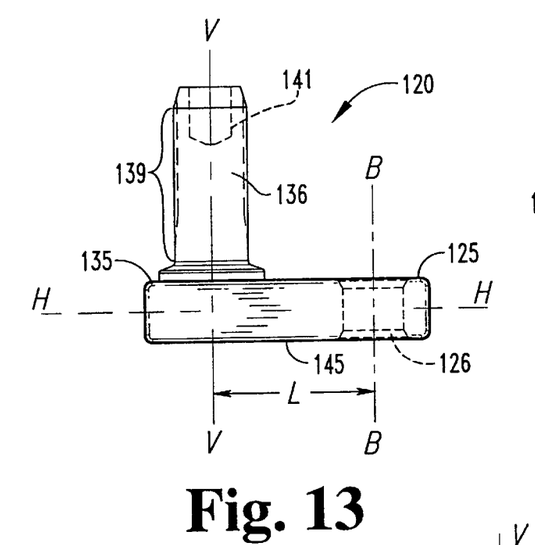
FIG. 13 is an elevational view of a bracket of this invention.
Figure 14:
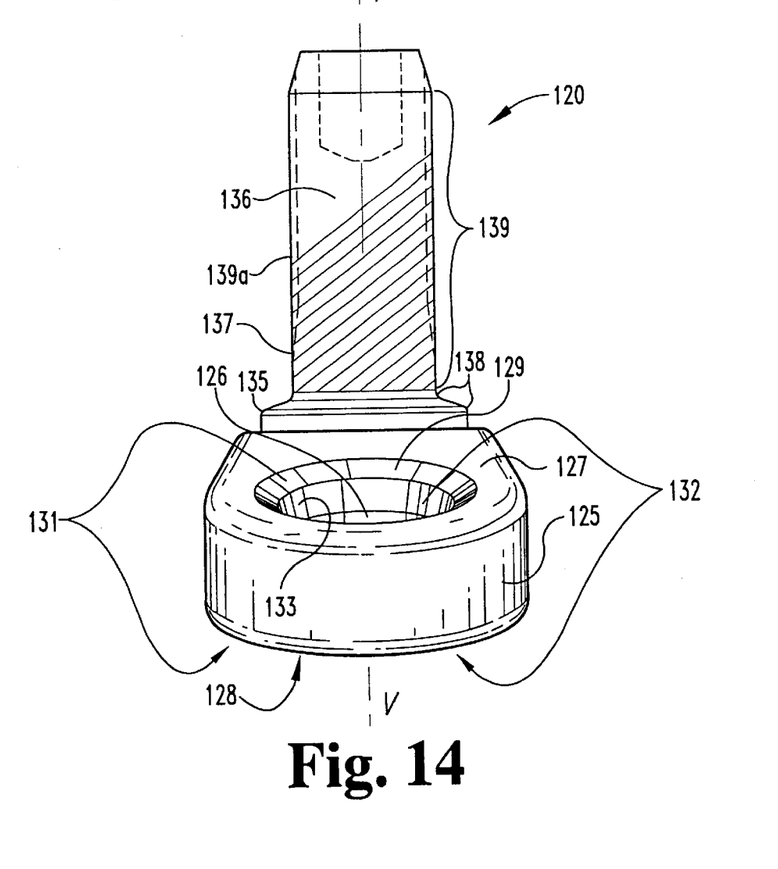
FIG. 14 is a side elevational view of the bracket.
Figure 15:
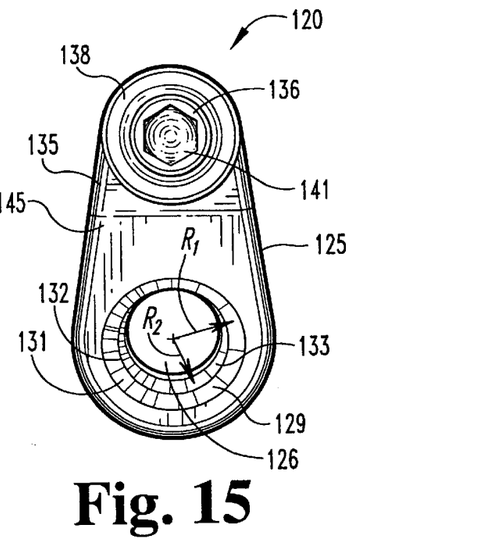
FIG. 15 is a top elevational view of the bracket.

The system 100 can include a bracket 120 for connecting the plate 101 to the bone. The bracket 120 includes a headpiece 125, a connector 135 laterally offset from the headpiece 125 and a lateral projection 145 extending outwardly from the headpiece 125 and attaching the headpiece 125 to the connector 135. Connector 135 includes a post 136 which is engageable to an aperture in the longitudinal member, such as the slot 104' shown in FIG. 11. Referring now to FIGS. 13–15, the headpiece 125 defines bore 126 for receiving a bone fastener such as bolt 110.

The connector 135 is configured to mate with an aperture in a spinal plate such as the ones depicted in FIGS. 10 and 11 herein. The post 136 of the connector 135 includes a first longitudinal member mating surface 137 for mating with an aperture such as the slot 104 or 104' in the plates shown in FIGS. 10 and 11. The mating surface 137 is sized to span the plate aperture and provide a substantial surface for stably supporting the bottom side 102 of the plate. The post 136 defines a vertical axis V which is perpendicular to a horizontal axis H defined by the connector 135. The connector 135 also includes a second longitudinal member mating surface 138 which is concentric with the post 136. The second mating surface 138 is preferably convex for mating engagement with a concave surface such as scallops 107 of the longitudinal member or plate 101. The post 136 of the connector 135 also includes a fastener engaging surface 139. Preferably, the fastener engaging surface 139 is provided with threads 139a for engaging an internally threaded fastener such as nut 150. The post 136 may also be provided with an aperture for receiving a driving tool such as an internal hex 141.

The headpiece 125 of the bracket 120 is provided to engage a bone fastener offset from the engagement of the bracket 120 with a spinal plate. The headpiece 125 includes a first face 127 and an opposite second face 128. A bore 126 defined to extend between the first face 127 and the second face 128. The headpiece 125 defines a bore axis B through the bore 126.

In preferred embodiments, the headpiece 125 further includes angulation means for variably angulating the bone fastener relative to the bore axis B. In one embodiment depicted in FIG. 14, the angulation means includes a first concave depression 129 defined in the first face 127 and concentric with the bore 126. The second concave depression (not shown) is preferably defined in the second face 128 also concentric with the bore 126. In a most preferred embodiment the angulation means includes first and second sets of nested concave depressions. The depressions of the first set 131 include the first concave depression 129 and another corresponding concave depression (not shown) on the opposite side 128. The second set of concave depressions includes a concave depression 132 which is concentric with the bore 126 and another corresponding concave depression (not shown) on the opposite face 128. The first set 131 has a spherical radius $R_1$ that is different from the radius $R_2$ of the second set 132. The second set 132 includes a second concave depression 133 defined in the first face 137 and a corresponding concave depression (not shown) on the opposite side 128. The angulation means in connection with the arcuate surface 116 of the bolt 110 allows the fastener 110 to angulate relative to the axis of the bore B at a particular angle $\alpha$. In this embodiment, a fastener is preferably provided which will engage the first portion 112 and one of the concave depressions 129 or 133.

Figure 16:
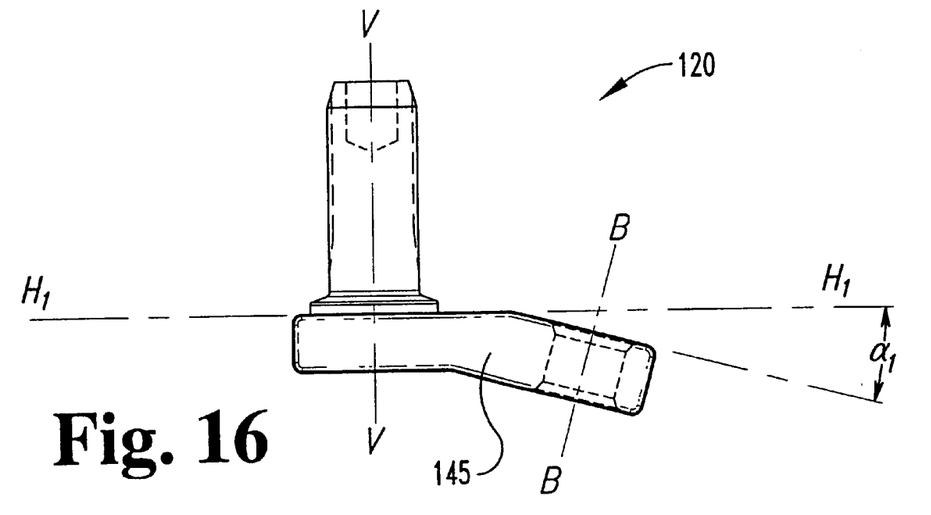
FIG. 16 is an elevational view of another embodiment of this invention.
Figure 17:
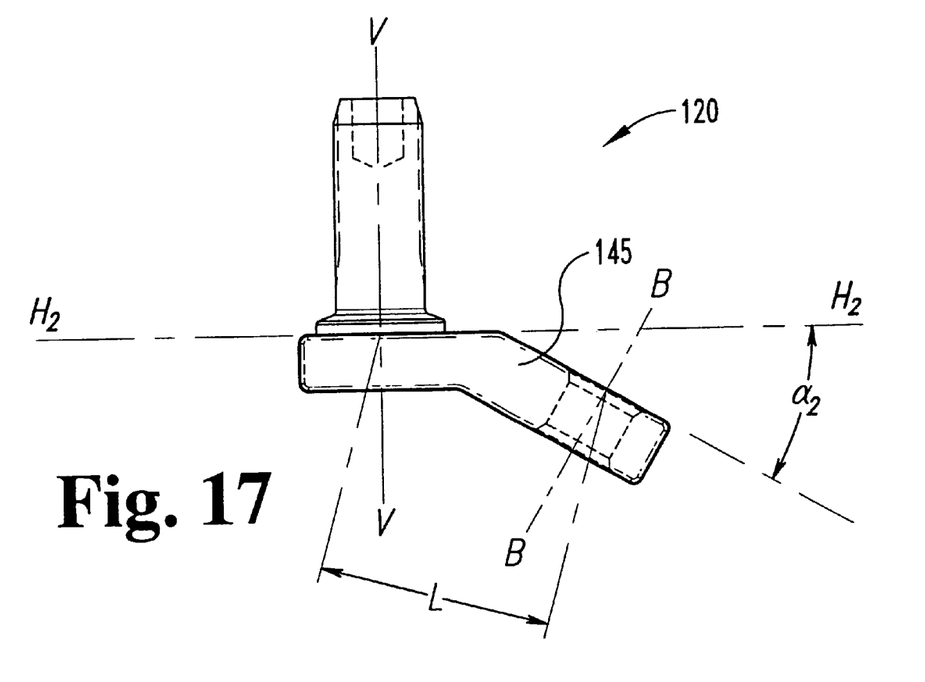
FIG. 17 is an elevational view of another embodiment of this invention.

The lateral projection 145 of the bracket 120 extends outwardly from the headpiece 125 and attaches headpiece 125 to connector 135. The lateral projection 145 also provides translational and angular adjustment. For lateral adjustment, the lateral projection 145 may have any suitable length so that the bracket 120 has a desired length L between the vertical axis V of the post and the bore axis B. In the embodiment depicted in FIG. 13 the lateral projection 145 is parallel with the horizontal axis H at 90° from the vertical axis V. In some preferred embodiments, the lateral projection 145 is angulated relative to the horizontal axis H at an angle in the range of about 2° to about 45°. Two such embodiments are depicted in FIGS. 16 and 17. In FIG. 16, the angulation angle $\alpha_1$ as related to the horizontal axis $H_1$ is about 15° and in FIG. 17 the angulation angle $\alpha_2$ relating to axis $H_2$ is about 30°.

Figure 18:
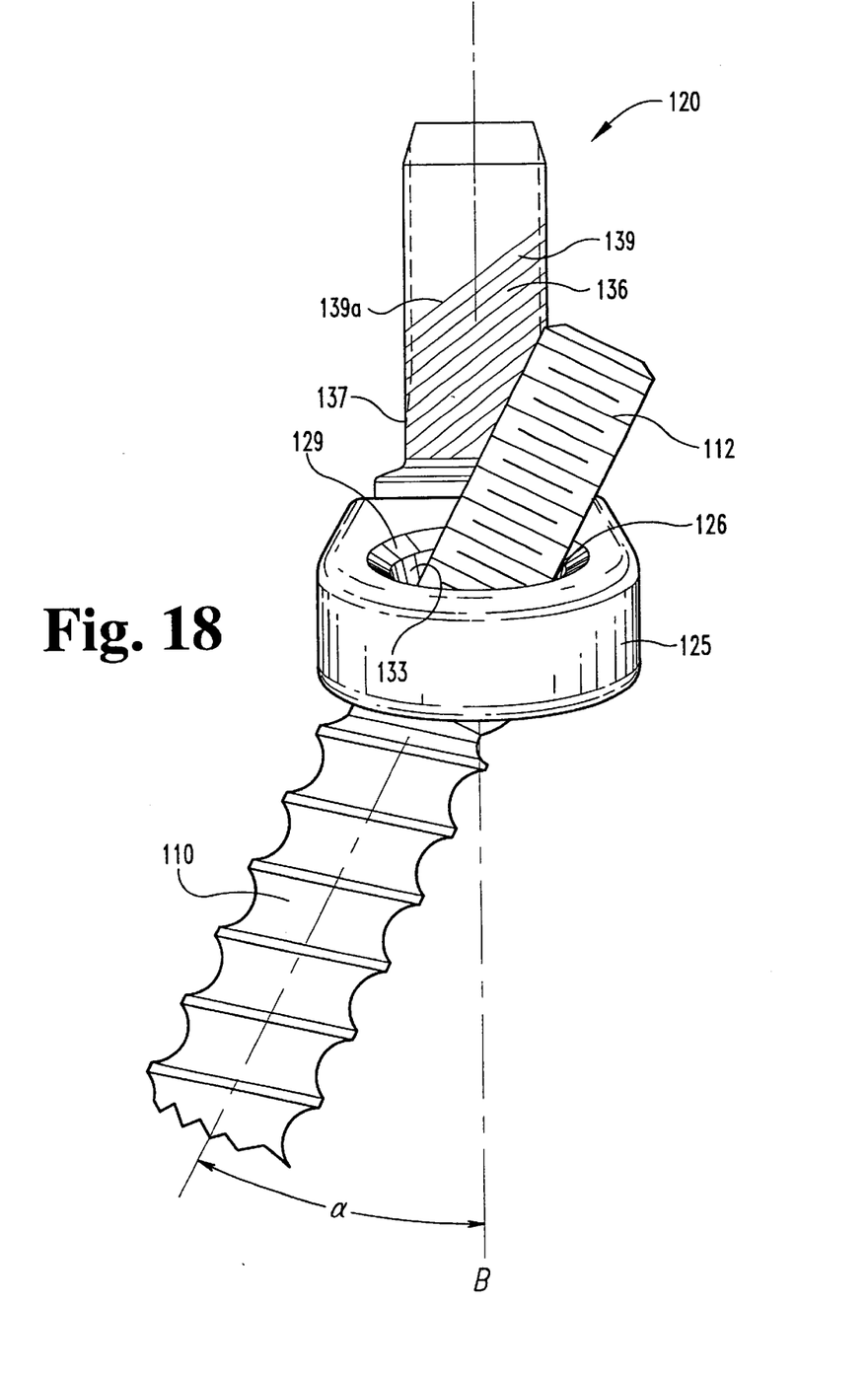
FIG. 18 is a side elevational view of a bracket and a bone fastener.

Referring now to FIGS. 13 and 18, when the angulation angle $\alpha$ of the lateral projection 145 is 0° from the vertical axis V, the bore axis B and the vertical axis v will be parallel. However, as shown in FIGS. 16 and 17 when the angulation angle $\alpha_1$ or $\alpha_2$ is anything other than 0° or 180° the vertical axis V and the bore axis B will no longer be parallel and will converge at some point. The combination of the angulation of the lateral projection 145, the variation in the distance L between the vertical axis and the bore axis along with the angulation means of the bore 126 of the headpiece 125 offer superior compensation for both translational and angular misalignment of bone fasteners relative to spinal plates. The differing lengths of the lateral projections 145 compensate for translational misalignment of bone bolts relative to spinal plates. The angulation of the lateral projection 145 compensates for angular misalignment of bone fasteners.

The invention also contemplates fasteners for both the threaded post 136 of the connector 135 and the first portion 112 of the bone bolt 110. Preferably, the fastener is an internally threaded nut 150 for mating engagement with threads 119 of the first portion 112 of the bolt and the threaded portion 139 of the post 136 of the connector 135. Preferably, the nut 150 is provided with a rigid lower arcuate surface 157 which is substantially complementary to the concave depressions 129 and 133 and is received within the concave depressions when the nut 150 is tightened down along the first threaded portion 112. The arcuate surface 157 will also preferably be complimentary with scallops 107 in the plate so that the nut 150 will be received within the scallops when the nut 150 is engaged to the threaded post and tightened down on the plate and within the scallops.

The invention also preferably includes various kits for spinal surgery. One of the kits includes a plurality of brackets, bone bolts and nuts. Another kit of this invention provides a plurality of brackets to be used with existing spinal systems such as the DYNALOK® or the DANEK® Plate System of Danek Medical, Inc. Using a kit of this invention, the surgeon will be provided with many options for fitting a spinal device such as a plate to a fixation member such as bone screw or a bone bolt. During the surgery, the surgeon can compensate for any translational and angular misalignment of the bone fasteners relative to the plate by simply using an appropriate bracket.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A kit for use in connecting an apertured spinal plate to a bone, comprising: a plurality of brackets, each bracket including;

a headpiece defining a bore for receiving a bone fastener;

a connector laterally offset from said headpiece and having a post defining a first longitudinal member mating surface for mating with an aperture in the longitudinal member, said post defining a vertical axis, said connector having a horizontal axis perpendicular to said vertical axis; and a lateral projection extending outwardly from said headpiece and attaching said headpiece to said connector, one of said brackets having a lateral projection that is parallel to said horizontal axis and another of said plurality of brackets having a lateral projection angulated relative to said horizontal axis.

2. The kit of claim 1 wherein said lateral projections have differing lengths among said plurality of brackets.

3. The kit of claim 2 further comprising angulation means for permitting angulation of the bone fastener relative to said bore axis of at least one of said brackets.

4. The system of claim 3 wherein said angulation means includes a first concave depression defined in said first face concentric with said bore and a second concave depression defined in said second face concentric with said bore.

5. A kit for use in connecting a spinal plate with a plurality of apertures to a bone, comprising:

a plurality of brackets, each bracket including;

a headpiece defining a bore for receiving a bone fastener;

a connector laterally offset from said headpiece and having a post defining a first mating surface for mating with a peripheral surface of an aperture, said post defining a vertical axis, said connector having a horizontal axis perpendicular to said vertical axis;

a lateral projection extending outwardly from said headpiece and attaching said headpiece to said connector, one of said brackets having a lateral projection that is parallel to said horizontal axis and another of said plurality of brackets having a lateral projection angulated relative to said horizontal axis, said lateral projections having differing lengths among said plurality of brackets; and wherein at least one of the apertures have a concave peripheral surface, and said connector includes a convex mating surface for mating engagement with the concave surface of an aperture.

6. The kit of claim 5 wherein the bore extends between a first face and a second face of said headpiece, said headpiece defining a bore axis through said bore, said first face defining a first concave depression concentric with said bore and said second face defining a second concave depression concentric with said bore.

7. The kit of claim 6 wherein each said first concave depression has a first spherical radius, said second concave depression has a second spherical radius, and said first spherical radius is different from said second spherical radius.

* * * * *